United States Patent
Cook

(10) Patent No.: US 7,063,678 B1
(45) Date of Patent: Jun. 20, 2006

(54) EXERCISE VEST FOR USE WITH AN UNWEIGHTING SYSTEM TO CORRECT A SCOLIOSIS CONDITION

(76) Inventor: Gerry Cook, 3115 N. Boyer Ave., Sandpoint, ID (US) 83864

( * ) Notice: Subject to any disclaimer, the term of this patent is extended or adjusted under 35 U.S.C. 154(b) by 187 days.

(21) Appl. No.: 10/916,220

(22) Filed: Aug. 11, 2004

Related U.S. Application Data

(60) Provisional application No. 60/494,258, filed on Aug. 11, 2003.

(51) Int. Cl.
*A61F 5/00* (2006.01)
*A63B 22/00* (2006.01)

(52) U.S. Cl. .................................................. 602/40
(58) Field of Classification Search .................. 602/19, 602/20, 32–40; 482/66–69; 128/28 R; 5/89.1, 5/600
See application file for complete search history.

(56) References Cited

U.S. PATENT DOCUMENTS

| | | | | |
|---|---|---|---|---|
| 4,202,327 A | | 5/1980 | Glancy | |
| 4,569,340 A | * | 2/1986 | Burton | 602/36 |
| 4,746,084 A | * | 5/1988 | Strong | 244/151 R |
| 5,033,460 A | * | 7/1991 | Goldish | 606/241 |
| 5,356,355 A | | 10/1994 | Campbell | |
| 5,462,518 A | | 10/1995 | Hatley et al. | |
| 5,626,540 A | | 5/1997 | Hall | |
| 5,662,560 A | * | 9/1997 | Svendsen et al. | 482/69 |
| 5,667,461 A | | 9/1997 | Hall | |
| 5,967,998 A | | 10/1999 | Modglin | |
| 6,273,844 B1 | | 8/2001 | Kelsey et al. | |
| 6,436,011 B1 | | 8/2002 | Cook | |

* cited by examiner

*Primary Examiner*—Henry Bennett
*Assistant Examiner*—Shumaya B. Ali

(57) ABSTRACT

An exercise vest including a waist band belt fitting around a user's mid-section adjacent the apex of the thoracic curve. A pair of shoulder straps for connecting the belt to an unweighting system. A weight transfer strap having one end secured to a shoulder strap belt on the side of the user opposite the apex of the thoracic curve. The free end of the weight transfer strap connected to the belt at a position on the user's back adjacent the apex of the thoracic curve. A loop attached to the belt for redirecting the strap in a direction such that the strap has a vector component extending laterally across the user's back. Finally, an ischial tuberosity strap is positioned to extend beneath the gluteous fold of the user and has each of its ends connected to the belt at the front of the user.

1 Claim, 6 Drawing Sheets

EXERCISE VEST FOR USE WITH AN UNWEIGHTING SYSTEM TO CORRECT A SCOLIOSIS CONDITION

This application claims the benefit of provisional application Ser. No 60/494,258 filed Aug. 11, 2003.

BACKGROUND OF INVENTION

The present invention relates to an exercise vest for use with an unweighting system to correct patient back problems such as a scoliosis condition.

A skeletal structure showing scoliosis of the spine is shown in FIG. 1. In this figure, spine "A" has a thoratic curve with an apex "B". The present invention relates to apparatus for forcing the apex of the thoratic curve in a direction to be aligned with the normal spine "A".

It is known in the art that spinal traction and stretching of the back can provide relief of a scoliosis condition. For example, U.S. Pat. No. 5,626,540 to Hall and U.S. Pat. No. 5,462,518 to Hatley et al. show traction assemblies which can be used to relieve a scoliosis condition. U.S. Pat. No. 4,202,327 to Glancy shows a device for correcting a scoliosis condition utilizing a rigid torso enveloping shell.

It is an object of the present invention to provide an exercise vest designed to correct a scoliosis condition by exerting a lateral force on the apex of the thoratic curve forcing the apex into alignment with the spine. The present invention is used in combination with a treadmill and a harness assembly for suspending a patient from a conventional unweighting system. With the present invention, forces are applied to the apex of the thoratic curve to correct the scoliosis condition.

SUMMARY OF INVENTION

The present invention is directed to a vest for correcting a scoliosis condition of the user's spine having a thoratic curve with an apex. The vest includes a waist band belt having two ends for connecting together around a user's mid-section adjacent the apex of the thoratic curve. A pair of shoulder straps are connected to the belt for connecting the belt to an unweighting system. A weight transfer strap is provided having one end secured to a shoulder strap at a position adjacent the belt on the side of the user opposite the apex of the thoratic curve. The weight transfer strap includes a connector for connecting the free end of the weight transfer strap to the belt at a position on the user's back adjacent the apex of the thoratic curve. A loop is also provided on the belt for redirecting the strap in a direction such that the strap has a vector component extending laterally across the user's back. Finally, an ischial tuberosity strap is positioned to extend beneath the gluteous fold of the user and has one end crossing over the front side and connected to the left side of the user and having the other end of the strap crossing on the front side connected to the belt on the right side of the user.

BRIEF DESCRIPTION OF THE DRAWINGS

In order that the invention may be clearly understood and readily carried into effect, a preferred embodiment of the invention will now be described, by way of example only, with reference to the accompanying drawings wherein.

DESCRIPTION OF A PREFERRED EMBODIMENT

Figure 2:
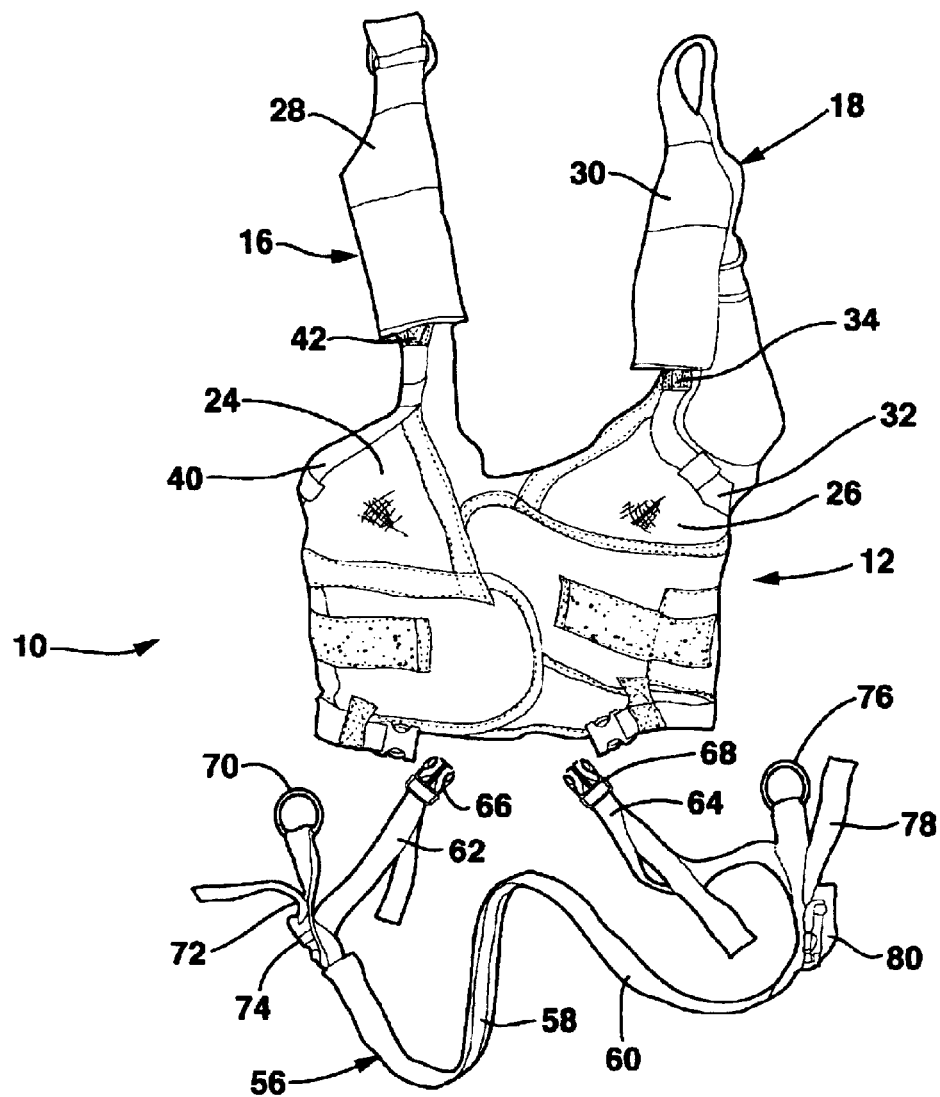
FIG. 2 is a front view of an exercise vest according to the present invention.
Figure 3:
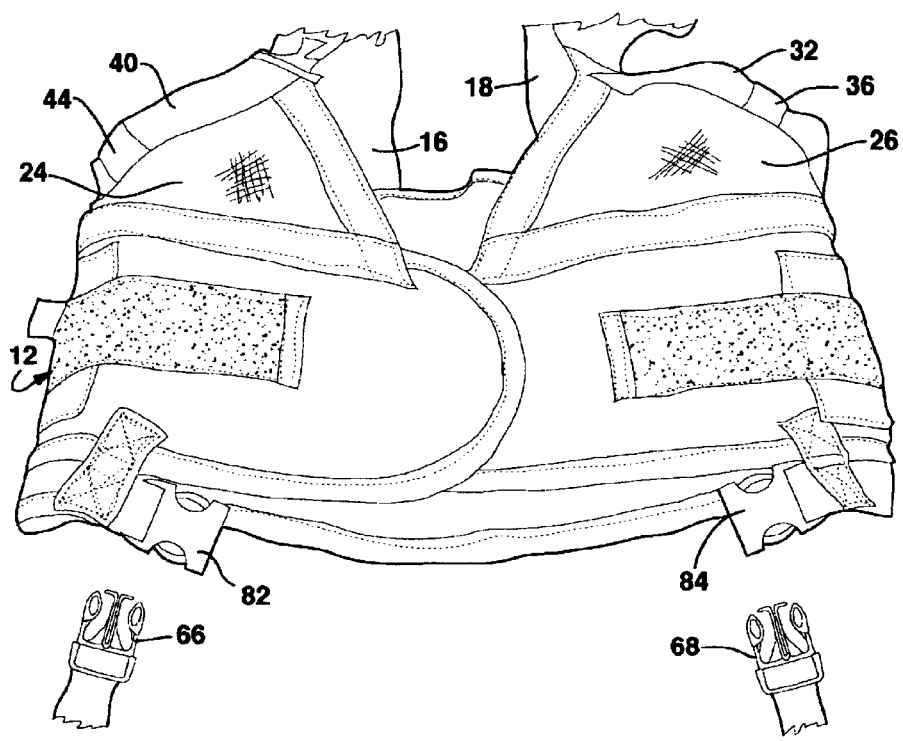
FIG. 3 is a detail front view of a waist band belt used with the present invention.
Figure 4:
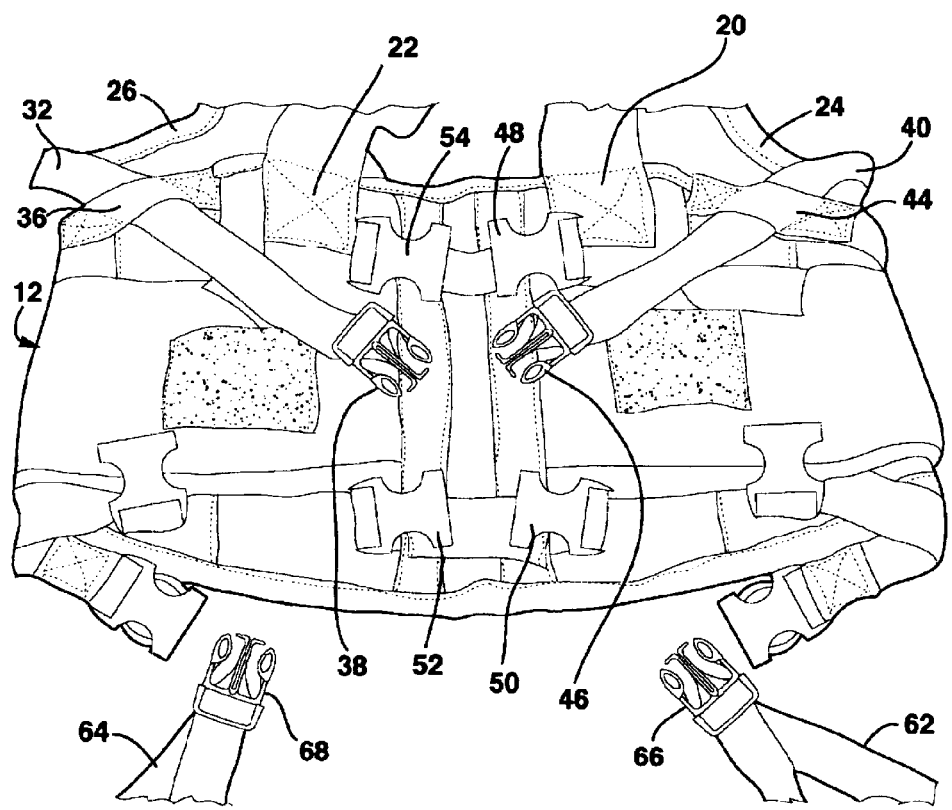
FIG. 4 is a detail rear view of the waist band belt shown in FIG. 3.

An exercise vest 10 according to the present invention is shown in FIGS. 2 through 4. The vest 10 includes a waist band belt 12 having two ends which may be fastened together as with a Velcro fastener, around the midsection of a user. A pair of shoulder straps 16 and 18 are attached to belt 12 for connecting the vest 10 to an unweighting system. The shoulder straps 16 and 18 have one end sewn to the back of waist belt 12 at 20 and 22, respectively, as shown in FIG. 4. The other end of each strap 16 and 18 is sewn to a triangular-shaped piece 24 and 26, respectively. The pieces 24 and 26 are, in turn, sewn to the front side of waist belt 12 as shown in FIG. 3. Each of the shoulder straps 16 and 18 are further provided with a shoulder pad 28 and 30, respectively.

A weight transfer strap 32 has one end sewn to shoulder strap 18 at 34, as shown in FIG. 2. The strap 32 is threaded through a force redirection loop 36 which is sewn to triangular piece 26, as shown in FIG. 3. A male buckle 38 is attached to the free end of strap 32, as shown in FIG. 4. Similarly, a weight transfer strap 40 has one end attached to shoulder strap 16 at 42, as shown in FIG. 2. The strap 40 extends through a force redirection loop 44 which is sewn to the triangular piece 24, as shown in FIG. 3. Further, the free end of strap 40 is provided with a male buckle 46.

On the backside of belt 12, four female buckles 48, 50, 52 and 54 are provided, as shown in FIG. 4. The female buckles 48–54 are used to receive the male buckles 38 and 46. The specific connection is dependent upon the particular use to be made of the vest 10.

An ischial tuberiosity strap 56 is shown in FIG. 2. The strap 56 is constructed of a nylon strap 58 sewn to a non-slip backing 60. An extension strap 62 is secured to one end of the nylon strap 58, and a second extension strap 64 is attached to the other end of nylon strap 58, as shown in FIG. 2. The extension strap 62 is connected to a conventional male buckle 66. The male buckle 66 has a pair of slots (not shown) to receive the extension strap 62 for adjusting the length of the extension strap 62. Similarly, the extension strap 64 is connected to a conventional male buckle 68, as shown in FIG. 2. Further, a ring 70 is held by a nylon strap 72 which is connected to a length adjusting buckle 74, as shown in FIG. 2. Similarly, a ring 76 is held by a strap 78 which is connected to a length adjusting buckle 80. Each of the straps 72 and 78 are secured to the nylon strap 58, as shown in FIG. 2.

The front of waist belt 12 is provided with a pair of female buckles 82 and 84, as shown in FIG. 3.

Figure 1:
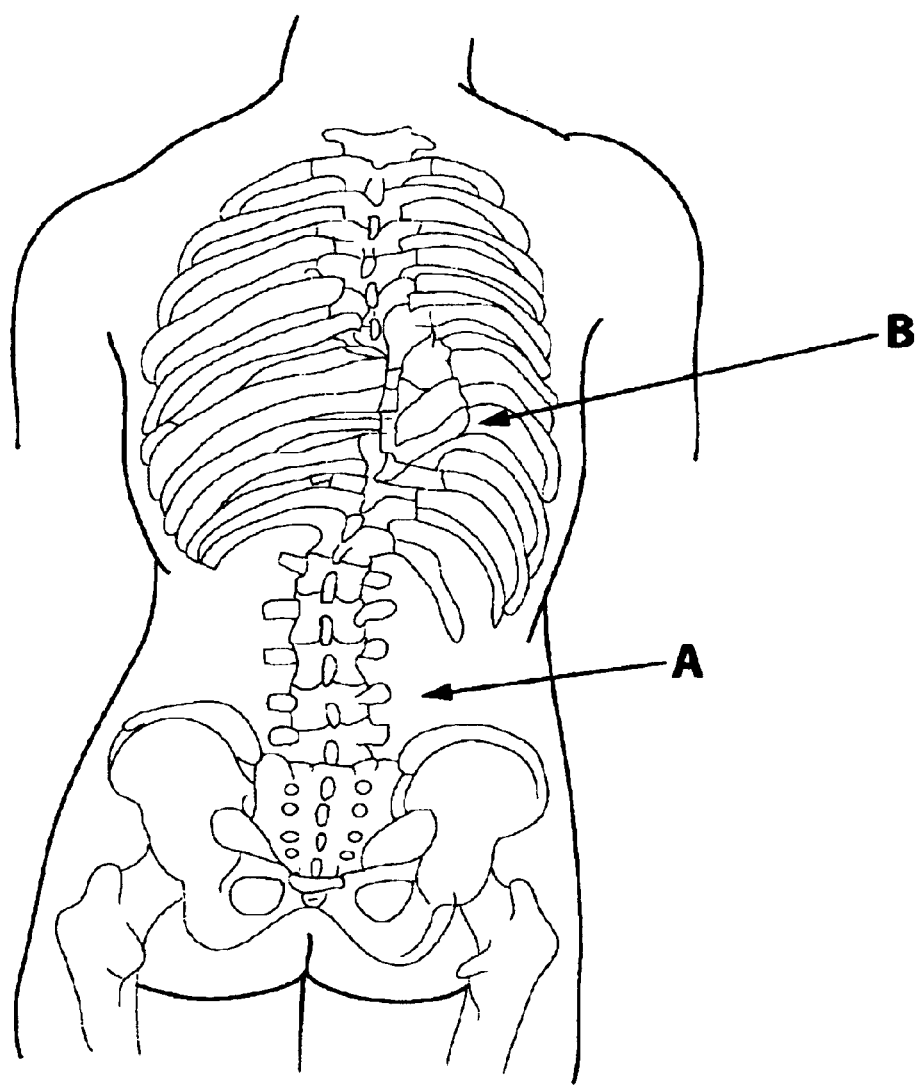
FIG. 1 is a front schematic view of a skeleton showing a scoliosis condition.
Figure 6:
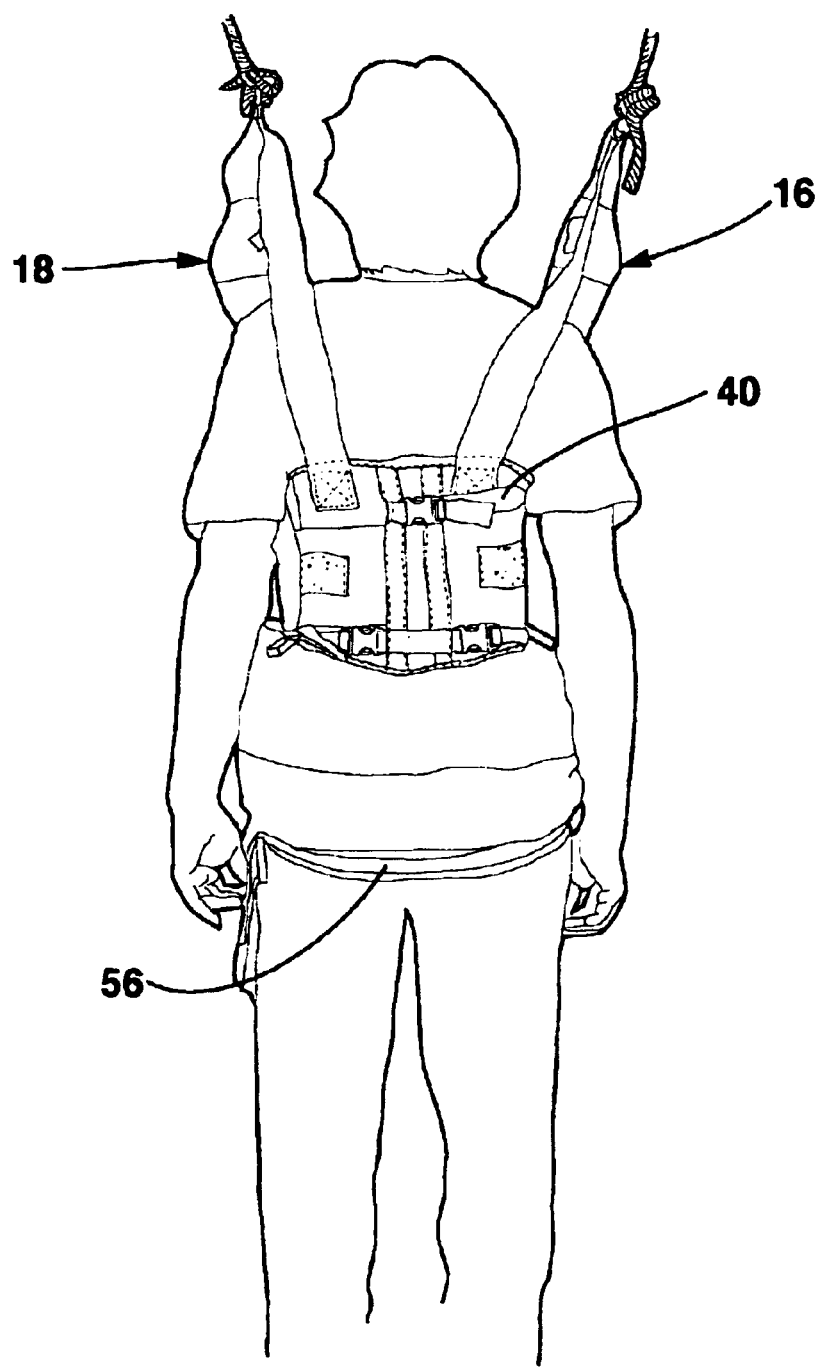
FIG. 6 is a rear view of the user wearing the exercise vest shown in FIG. 5.

In using the present invention, the shoulder straps 16 and 18 are hung from an unweighting system which may be positioned over a treadmill. The unweighting system is adjusted to be positioned so that the vest 10 may be fitted on the person using the treadmill. Next, the person is faced so that the person can back into the vest 10. The right arm is positioned through the right shoulder strap 16, and the left arm is positioned through the left shoulder strap 18. One of the weight transfer straps 32 or 40 is then connected to the appropriate female buckles 48–54 to align the strap with the apex of the thoratic curve. As an example, if the thoratic curve is to the left as shown in FIG. 1 the right hand weight transfer strap 40 is secured to either buckle 52 or 54 depending on which buckle is closest to the apex of the thoratic curve as shown in FIG. 6. If the curvature is to the right then the weight transfer strap 32 is connected to either the buckle 48 or 50 depending on which buckle is closest to the apex of the thoratic curve.

The front of the vest is then connected together with a Velcro strap provided with the waist belt 12 as shown in FIG. 3. The weight transfer strap being used is then pulled to provide the proper tension on the waist belt.

Figure 5:
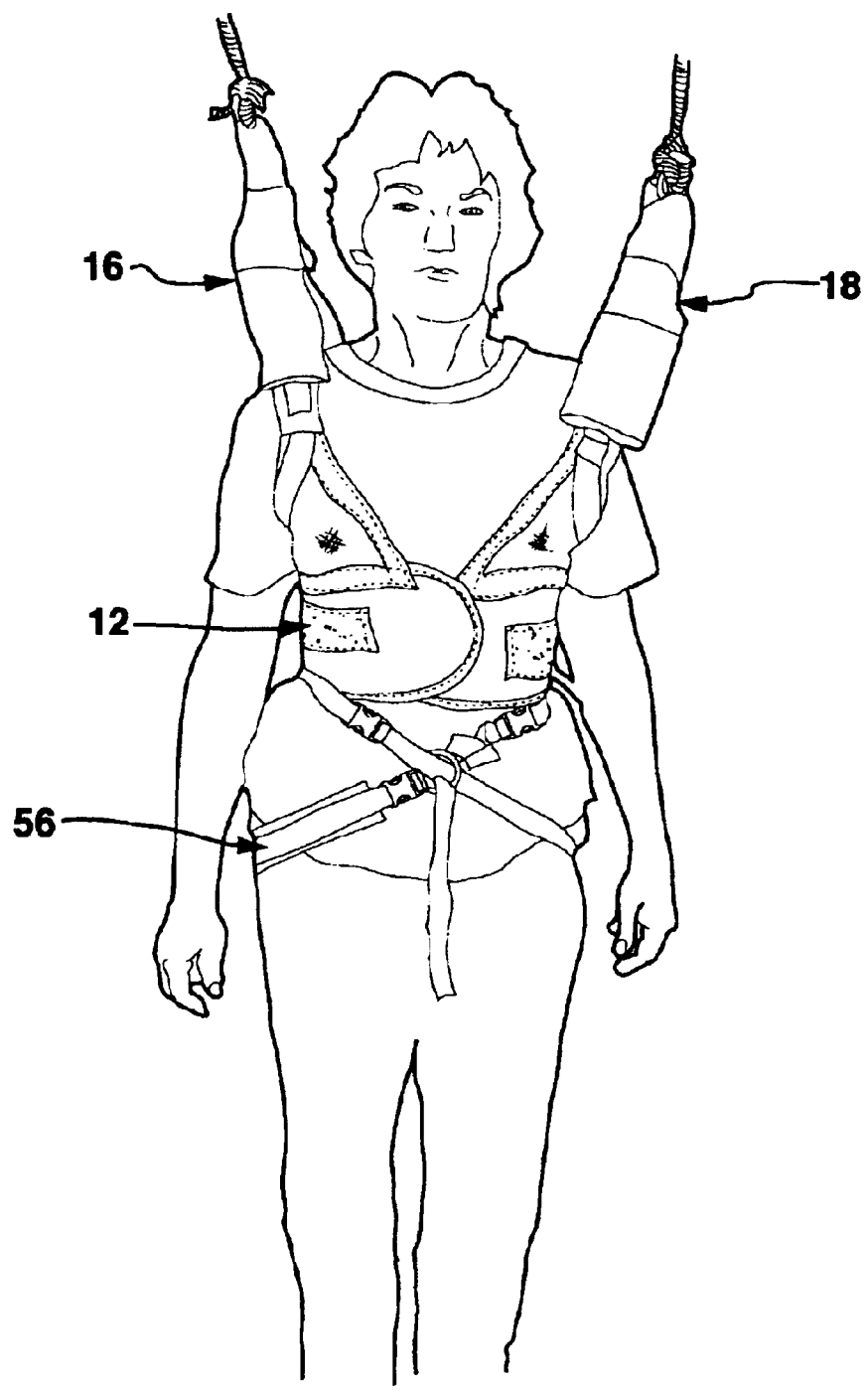
FIG. 5 is a front view of a user wearing the exercise vest shown in FIG. 2.

Next, the male buckle 66 connected to the ischial tuberosity strap 56 is snapped into the female buckle 84. The strap 56 is then drawn left to right, across the front, and wrapped around the right side and then the back of the patient. The free end of strap 56 is then threaded through the ring 70, and then the male buckle 68 is snapped into female buckle 82 as shown in FIGS. 5 and 6. The ischial tuberosity strap 56 is then slid up so that it is positioned at the gluteus fold. The extension straps 62 and 64 are then adjusted in length to maintain the strap at this position. Using the strap 78 with the adjustment buckle 80, the ring 76 is positioned approximately three and one-half inches (3½") above the rear position of the ischial tuberosity strap 56. This allows for a correct combination of horizontal and vertical vector components to correct a scoliosis condition. The strap 56 serves to support most of the weight of the user during exercising.

With this arrangement of the weight transfer straps 32 or 40 and the ischial tuberosity strap 56, the unweighting system is used to lift the user through strap 56 and either weight transfer strap 32 or strap 40. A vertical force vector is directed upwardly through the shoulder straps 16 and 18 to the unweighting system. The vertically upward vector is directed through the weight transfer strap 32 or 40 (whichever strap is being used) through the appropriate force redirection loop 36 or 44 to the apex of the thoratic curve as shown in FIG. 1. The force redirection loops 36 and 44 redirect the force being transferred by the weight transfer straps 32 and 40 to provide a vector in the lateral direction. The weight transfer straps 32 and 40 thus force the apex of the thoratic curve in a direction to be aligned with the normal spine "A" of the user as shown in FIG. 1.

While the fundamental novel features of the invention have been shown and described, it should be understood that various substitutions, modifications, and variations may be made by those skilled in the art, without departing from the spirit or scope of the invention. Accordingly, all such modifications or variations are included in the scope of the invention as defined by the following claims:

I Claim:

1. A vest for correcting a scoliosis condition of a user's spine having a thoratic curve with an apex comprising:

a band belt having two ends for fitting around the user's mid-section adjacent the apex of the thoratic curve and means for connecting the two ends together at the user's front side;

a pair of shoulder straps connected to the belt on a right and left side of the belt for connecting the belt to an unweighting system;

a weight transfer strap having one end secured to a shoulder strap at a position adjacent the belt on the side of the user opposite the apex of the thoratic curve;

the weight transfer strap having means for connecting the free end of the weight transfer strap to the belt at a position on the user's back adjacent the apex of the thoratic curve;

means for redirecting the strap in a direction having a vector component extending laterally across the user's back; and an ischial tuberosity strap positioned to extend beneath the gluteous fold of the user and having one end crossing over the front side of the belt and connected to the belt on the left side and having the other end of the strap crossing on the front side of the belt and connected to the belt on the right side of the belt.

* * * * *